US006306413B1

(12) United States Patent
Payne

(10) Patent No.: US 6,306,413 B1
(45) Date of Patent: Oct. 23, 2001

(54) STABLE AQUEOUS FORMULATION AND USE

(75) Inventor: John David Payne, Rossendale (GB)

(73) Assignee: Zeneca Limited, London (GB)

( * ) Notice: Subject to any disclaimer, the term of this patent is extended or adjusted under 35 U.S.C. 154(b) by 741 days.

(21) Appl. No.: 08/564,193

(22) PCT Filed: May 27, 1994

(86) PCT No.: PCT/GB94/01155

§ 371 Date: Dec. 18, 1995

§ 102(e) Date: Dec. 18, 1995

(87) PCT Pub. No.: WO94/16564

PCT Pub. Date: Aug. 4, 1994

(30) Foreign Application Priority Data

Jun. 18, 1993 (GB) .................................................. 9312645

(51) Int. Cl.⁷ .................................................. A01N 43/80
(52) U.S. Cl. ........................................... 424/405; 514/373
(58) Field of Search ............................ 424/405; 514/373

(56) References Cited

U.S. PATENT DOCUMENTS 3,726,970 * 4/1973 Weisse .................................. 424/656
5,125,967 * 6/1992 Morpeth ........................... 106/18.22

FOREIGN PATENT DOCUMENTS

| 243 616 | 11/1987 | (EP) . |
| 1191253 | 5/1970 | (GB) . |
| 94/16564 | 8/1994 | (WO) . |

OTHER PUBLICATIONS

Patent Abstract of Japan. vol. 015, No.031, (C–0798) Jan. 24,1991, & JP,A,02 268 900, Nov. 2, 1990 & Chemical Abstracts, vol. 114, No. 22, Jun. 3, 1991, abstract No. 213751e, Furokawa, et al"Deodorant composition for sludge", see abstract.

* cited by examiner

*Primary Examiner*—Peter F. Kulkosky
(74) *Attorney, Agent, or Firm*—Pillsbury Winthrop LLP

(57) ABSTRACT

Stable aqueous dispersions of 1,2-benzisothiazolin-3-one containing Xanthan gum which is substantially free from organic solvents.

14 Claims, No Drawings

STABLE AQUEOUS FORMULATION AND USE

This application claims benefit of international application PCT/GB94/01155, filed May 27, 1994.

The present invention relates to a stable aqueous formulation of 1,2-benzisothiazolin-3-one which is substantially free from organic solvents. 1,2-benzisothiazolin-3-one (hereinafter referred to as BIT) is an established industrial biocide and is particularly effective in protecting aqueous media against microbiological spoilage. It is particularly effective as a bactericide and is especially suited to the protection of latices. Thus, one of its major uses is as an in can preservative for the preservation of acrylic and acrylate paint emulsions.

BIT has low aqueous solubility and can cause sensitisation in some individuals. Consequently, for ease of handling and to reduce the risk of sensitisation,.BIT is generally formulated as a liquid composition. These compositions include stable solutions of BIT in an amine solvent as disclosed in UK 1,191,253 and UK 1,330,531, and also solutions of BIT in propylene glycol or diethylene glycol. None of these compositions are ideal and have never been wholly successful in commercial terms.

Because of the low aqueous solubility of BIT, an alternative approach to stable aqueous solutions has been to form the alkali metal salt of BIT, especially the sodium or lithium salt. The lithium salt of BIT is disclosed in U.S. Pat. No. 4,871,754 as having an aqueous solubility above 16% by weight which is approximately twice that of the sodium salt of BIT. The lithium salt of BIT is, however, more expensive to manufacture. Other approaches to increasing the aqueous solubility of the sodium salt of BIT is to include co-solvents such as dipropylene glycol as disclosed in U.S. Pat. No. 4,188,376 or urea as disclosed in U.S. Pat. No. 4,751,311. The formulation containing dipropylene glycol has become extremely important commercially. However, formulations containing the alkali metal salt of BIT exhibit relatively high pH which is a disadvantage in some applications. Furthermore, there is an every increasing demand for formulations containing a low concentration of volatile organic compounds (hereafter VOC). Hence, formulations containing solvents such as glycols are becoming less acceptable.

Because of its low aqueous solubility, BIT has also been formulated as a dispersion wherein the BIT is generally dispersed by means of a non-ionic or anionic surface active agent. Aqueous dispersions containing 33% by weight BIT are known, but tend to be unstable under storage at elevated temperature resulting in gels which are difficult to handle. Improved dispersions have been attempted by incorporating solvents such as propylene glycol, but such dispersions tend to layer and separate on storage at elevated temperature and the BIT consequently aggregates and forms lumps. Alternatively, mineral clays have been included in the formulation to structure the aqueous phase with the objection of inhibiting separation. This tends to reduce aggregation of the BIT but the formulation again separates on storage at elevated temperature. As with the formulations containing solvents, the formulations containing clays require rehomogenising prior to use and this can be difficult and expensive. Failure to ensure uniform distributon of the BIT throughout the formulation can given rise to errors in metering and subsequent reduction, or even loss, of microbial protection in the media to be preserved.

Xanthan gum is a polysaccharide thickener which forms a structured network of entangled molecules in water which aids the suspension of particulate matter, and can reduce sedimentation. Aqueous dispersions containing 33% by weight BIT have been prepared containing both a Xanthan gum and propylene glycol as a cosolvent. Again such formulations tend to separate and the BIT tends to aggregate and form lumps. The addition of glycols such as mono- and dipropylene glycol to aqueous formulations generally increases the viscosity of the formulation as disclosed in Examples 16 to 21 of UK Patent Application No. 9300936.3. which relates to aqueous solutions of the sodium salt of BIT. The more dipropylene glycol is added, the higher the viscosity. We have now surprisingly found that when the propylene glycol is removed from aqueous formulations containing BIT dispersed in the presence of Xanthan gum and the glycol, the viscosity actually increases. This observation is contrary to the effect of the glycol observed in the formulations disclosed in UK Patent Application No. 9300936.3. As a result, we have now found it possible to make a stable aqueous formulation of BIT in the presence of a Xanthan gum which is substantially free from organic solvents.

According to the present invention there is provided a stable aqueous formulation comprising from 5 to 30% by weight microbiologically active agent containing at least 50% BIT, from 1 to 4% dispersant and from 0.1 to 0.5% by weight Xanthan gum, which formulation is substantially free from organic solvents.

The remainder of the aqueous formulation is preferably wholly water but may comprise other materials, such as inorganic salts. The formulation, is however, preferably, completely free from organic solvents.

Preferably, the amount of microbiologically active agent in the formulation is at least 7% and more preferably at least 9%, for example 10% by weight of the formulation. The amount of microbiologically active agent is also preferably less than 25% and more preferably less than 22%, for example 20% by weight of the formulation.

The dispersant is preferably either non-ionic or anionic, or a mixture thereof, but is especially anionic. Examples of suitable nonionic dispersants are condensates of ethylene oxide or propylene oxide including block co-polymers of ethylene oxide and propylene oxide. Examples of suitable anionic agents are sodium lignin sulphonate and the sodium salt of naphthalene sulphonic acid/formaldehyde condensates. Mixtures of anionic and non-ionic dispersants may also be used. Preferably the amount of dispersant is at least 1.2% and especially at least 1.5% by weight relative to the total formulation. It is preferred that the amount of dispersant is less than 3.5%, for example 3% by weight of the total formulation.

The amount of dispersant is commonly calculated on the amount of microbiologically active agent in the formulation. Thus, the ratio of dispersant to microbiologically active agent is preferably 1:20, more preferably 2:20 and especially 3:20.

The amount of Xanthan gum is preferably at least 0.2%, more preferably at least 0.3% and especially at least 0.35% relative to the total weight of the formulation. It is also preferred that the amount of Xanthan gum is less than 0.45%, for example 0.4 relative to the total weight of the composition.

The pH of the formulation may be from 1 to 8 but is preferably above 3, more preferably above 5 and especially above 6. It is especially preferred that the pH is about neutral, i.e. from 6.5 to 7.5 but more preferably is not greater than 7.

As noted hereinbefore, the exclusion of the glycol solvent from formulations of BIT containing a dispersant, Xanthan gum and propylene glycol results in an increase in viscosity. The formulations of the present invention preferably exhibit a viscosity of at least 1000, preferably at least 1200 and especially at least 1500 centipoise as measured by Brookfield viscometer using Spindle No. 2 and rotational speed of 10 rpm. The viscosity is preferably less than 3,500 and especially less than 3000 centipoise.

We have obtained a particularly stable dispersion containing about 20% by weight.BIT, about 3% anionic dispersant and 0.3 to 0.4% Xanthan gum relative to the total weight of the formulation, the remainder being water.

The formulation preferably contains BIT as the only microbiologically active agent, but it may contain one or more further microbiologically active agent. The further microbiologically active agent is preferably one which extends the spectrum of activity against micro-organisms. When the composition contains more than one microbiologically active agent, the further microbiologically active agent or agents may be added to the formulation simultaneously with the BIT or may be added sequentially.

The further microbiologically active agent may be present in up to the same amount as BIT, but is more preferably less. Thus, according to a further aspect of the invention there is provided an aqueous formulation comprising from 2.5% to 15% by weight BIT, from 2.5% to 15% by weight of a further microbiologically active agent, from 1 to 4% dispersant and from 0.1 to 0.5% by weight Xanthan gum. Preferably, the further microbiologically active agent is equal to the amount of BIT, and is especially about two thirds the amount of BIT.

Preferably the further microbiological agent is the 2:1 Zinc complex of 2-mercaptopyridine-1-oxide.

We have obtained a further especially stable dispersion where the microbiologically active agent comprises 12.3% BIT and 7.7% of the 2:1 zinc complex of 2-mercaptopyridine-1-oxide.

The formulation containing BIT may be made from an aqueous paste of BIT such as that resulting from the filtration of BIT in a filter press (hereafter referred to as 'press paste') which is a filter cake containing BIT itself and water with substantially no other adjutants. The press paste typically contains from 70 to 80% BIT and has a pH of between 6 and 7.2. Typically, the dispersant is dissolved in water and the BIT press paste added over a period of time, generally 1–2 hours at 20–25° C. in a high shear mixer to disperse the BIT throughout the aqueous phase. Any foaming can be controlled in conventional manner by adding a suitable anti-foam agent which is compatible with other components of the formulation and which does not interfere with the microbiological activity of the BIT or the further microbiologically active agent, if present. The suspension is then milled until the dispersed matter has a particle size below 20 $\mu$, preferably below 10 $\mu$ and especially below 5$\mu$. The remainder of the water is then added followed by the Xanthan gum, which is preferably added as a solid. Addition of the Xanthan gum is made under rapid agitation in order to prevent the formulation of lumps.

The formulations of the present invention are microbiologically active and can be used as industrial biocides to protect media against microbiological deterioration.

The invention is further illustrated by the following non-limiting examples wherein all references to amounts are in parts by weight unless stated to the contrary.

EXAMPLE 1

Sodium lignin sulphonate (30 parts) is dissolved in water (350 parts) by stirring at 20–25° C. BIT press paste (266 parts containing 75% BIT and 25% water) was added over 30 minutes and uniformly distributed in a Silverson mixer. The resulting dispersion was then milled in a horizontal bead mill in the presence of Ballotini beads until a mean-particle size of 95% BIT below 5$\mu$ was obtained. The remainder of the water was then added followed by Xanthan gum (4 parts) which was added as a dry powder over 30 minutes. The formulation obtained contained 20% BIT, 3% dispersant and 0.4% Xanthan gum, the remainder being water. It had a viscosity of about 3100 centipoise as measured by Brookfield viscometer using Spindle No 2 and a rotation speed of 10 rpm.

The formulation exhibited excellent stability when stored at 40° C. for 1 month with only about 1% separation.

Comparative Example A

Example 1 was repeated except that 10% of the water was replaced by an equivalent amount of dipropylene glycol. The viscosity of the resultant formulation was reduced to about 1650 centipoise. This is contrary to the effect of adding dipropylene glycol to aqueous solutions of the sodium salt of BIT as disclosed in UK Application No. 930936.3.

EXAMPLE 2

Example 1 was repeated except that the amount of sodium lignin sulphonate and the amount of BIT press paste was reduced by 50% with consequential adjustment to the amount of water. The resulting formulation contained 10% PIT, 1.5% dispersant and 0.4% Xanthan gum, the remainder being water. When stored for 1 month at 40° C., the formulation showed no separation.

EXAMPLE 3

Sodium lignin sulphonate (15 parts) was dispersed in water (200 parts) by stirring at 20–25° C. BIT press paste (168 parts containing 73.6% BIT) was added and dispersed uniformly throughout the aqueous phase by mixing for 10 minutes in a Silverson mixer.

The course dispersion so obtained was then milled in a horizontal bead mill in-the presence of Ballotini beads and with a peripheral disc speed of about 1500 ft/min. Milling was continued until the mean particle size of the BIT has a distribution of 95% below 5 $\mu$.

An aqueous dispersion of the 2:1 zinc complex of 2-mercaptopyridine-1-oxide (160 parts; ex Olin Chem. Co., USA) together with the remaining water was added and thoroughly mixed.

Xanthan gum (5 parts) was then added rapidly under high shear mixing and mixing continued for a further 20 minutes. The resulting formulation contained 12.3% BIT, 2.0% dispersant, 7.7% 2:1 zinc complex of 2-mercaptopyridine-1-oxide and 0.5% Xanthan gum, the remainder being water. The formulation exhibited excellent stability when stored for 1 month at 40° C. with no observable phase separation.

What is claimed is:

1. A stable aqueous formulation comprising from 5 to 30% by weight of a microbiologically active agent containing at least 50% BIT, from 1 to 4 dispersant and from 0.1 to 0.5% by weight Xanthan gum, which formulation is substantially free from organic solvents.

2. A formulation as claimed in claim 1 wherein the remainder of the formulation is water.

3. A formulation as claimed in either claim 1 or claim 2 wherein the amount of microbiological agent is at least 9% by weight of the total formulation.

4. A formulation as claimed in claim 1 wherein the amount of microbiological agent is less than 22% by weight of the total formulation.

5. A formulation as claimed in claim 1 which contains only BIT as the sole microbiologically active agent.

6. A formulation as claimed in claim 1 which has a viscosity of at least 1000 centipoise.

7. A formulation as claimed in claim 1 which has a viscosity of less than 3500 centipoise.

8. A formulation as claimed in claim 1 which comprises about 20% BIT, about 3% dispersant and about 0.4% Xanthan gum by weight of the total formulation.

9. A formulation as claimed in claim 1 which comprises about 10% BIT, about 1.5% dispersant and about 0.4% Xanthan gum by weight of the total formulation.

10. A formulation as claimed in claim 1 which comprises about 12.3% BIT, about 2.0% dispersant, about 7.7% of the 2:1 zinc complex of 2-mercaptopyridine-1-oxide and about 0.4% Xanthan gum.

11. A formulation as claimed in claim 1 wherein the dispersant is anionic.

12. A formulation as claimed in claim 11 wherein the dispersant is sodium lignin sulphonate.

13. A formulation as claimed in claim 1 wherein the dispersant is a condensate of ethylene oxide or propylene oxide or a block co-polymer of ethylene oxide or propylene oxide.

14. A formulation as claimed in claim 1 wherein the microbiologically active agent is milled in the presence of the dispersant.

* * * * *

UNITED STATES PATENT AND TRADEMARK OFFICE
CERTIFICATE OF CORRECTION

PATENT NO.    : 6,306,413 B1                                            Page 1 of 1
DATED         : October 23, 2001
INVENTOR(S)   : Payne It is certified that error appears in the above-identified patent and that said Letters Patent is hereby corrected as shown below:

<u>Title page,</u>
Insert -- [*] Notice: Under 35 U.S.C. 154(b), the term of this patent shall be extended for 0 days. --.

Signed and Sealed this

Third Day of December, 2002

JAMES E. ROGAN
*Director of the United States Patent and Trademark Office*